United States Patent [19]

Zare et al.

[11] Patent Number: 4,675,300

[45] Date of Patent: Jun. 23, 1987

[54] LASER-EXCITATION FLUORESCENCE DETECTION ELECTROKINETIC SEPARATION

[75] Inventors: Richard N. Zare, Stanford, Calif.; Ernst Gassmann, Basel, Switzerland

[73] Assignee: The Board of Trustees of the Leland Stanford Junior University, Stanford, Calif.

[21] Appl. No.: 777,179

[22] Filed: Sep. 18, 1985

[51] Int. Cl.[4] .................................... G01N 21/76
[52] U.S. Cl. .......................... 436/172; 204/180.1; 356/344
[58] Field of Search .............. 204/180.1; 356/317, 356/318, 344; 436/89, 161, 172; 73/61.1

[56] References Cited

U.S. PATENT DOCUMENTS

| | | | |
|---|---|---|---|
| 4,008,397 | 2/1977 | Zdrodowski | 356/317 X |
| 4,135,816 | 1/1979 | Niemann et al. | 356/317 |
| 4,146,454 | 3/1979 | Haber | 204/180.1 X |
| 4,154,669 | 5/1979 | Goetz | 204/180.1 X |
| 4,233,030 | 11/1980 | Twitchell et al. | 73/61.1 C X |
| 4,331,590 | 5/1982 | Bocuslaski et al. | 260/112 B |
| 4,366,241 | 12/1982 | Tom et al. | 435/7 |
| 4,569,592 | 2/1986 | Osada et al. | 356/318 |

FOREIGN PATENT DOCUMENTS 2838760  3/1980  Fed. Rep. of Germany ...... 436/161

OTHER PUBLICATIONS

International Application Number WO79/00834 published Oct. 18, 1979.
Pretorius, V., et al., J of Chromatography, 99 (1974) 23–30.
Jorgenson, J. W., et al., J of Chromatography, 218 (1981) 209–216
Jorgenson, J. W., et al., Anal Chem., vol. 53, No. 8, Jul. 1981, 1298–1302.
Jorgenson, J. W., et al., Science, Vol. 222 (1983) 266–272.
Tsuda, T., et al., J. of Chromatography, 248 (1982) 241–247.
Tsuda, T., et al., J. of Chromatography, 264 (1983) 385–382.
David, P. A., et al., "Capillary Zone Electrophoresis: Instrumentation and Use with Nonaqueous Solvents", Oak Ridge Nat'l Laboratory, Apr. 1984.
Jorgenson, J. W., Science, vol. 226 (1984) 254–261.
Kuo, J. E., et al., Clin Chem., vol. 31, No. 1, 1985, 50–53.
McGuffin, et al. "Femtomole Analysis of Prostaglandin Pharmaceuticals" Dept. of Chem., Michigan State Univ., 7/30/85.
Halfman, C. J., et al., Anal Chem, 1985, 57, 1928–1930.
Jolley, M. E., J of Analytical Toxicology, vol. 5, Sep.-/Oct. 1981, 236–240.
Rice, C. L., et al., J Phys Chem, vol. 69, No. 11, 1965, 4017–4024.
Guthrie, E. J., et al., Anal Chem, 1984, 56, 483–486.
Small, H., et al., Anal Chem, 1982, 54, 564–469.
Martin, M., et al., Anal Chem., 1984, 56, 614–620.
Martin, M., et al., Anal Chem, 1985, 57, 559–561.
Jorgenson, J. W., et al., J of Chromatography, 255 (1983) 335–348.
Terabe, S., et al., Anal Chem., 1984, 56, 111–113.
Terabe, S., et al., Anal Chem., 1985, 57, 834–841.
Mikkers, J Chromatography, 1979, 169, 11.
Stevens and Cortes, *Anal. Chem.* 55, 1365–70 (1983).

Primary Examiner—Charles Hart
Attorney, Agent, or Firm—Ciotti & Murashige

[57] ABSTRACT

An electrokinetic process and apparatus employing coherent radiation-excited fluorescence for detection is disclosed. In a preferred embodiment, the support liquid is a chiral liquid and the process is employed to separate and detect the separation of optical isomers.

20 Claims, 6 Drawing Figures

LASER-EXCITATION FLUORESCENCE DETECTION ELECTROKINETIC SEPARATION

BACKGROUND OF THE INVENTION

1. Field of the Invention

This invention relates to the field of electrophoresis. More particularly, it concerns an improved process and apparatus for carrying out and detecting electrokinetic separations in open-tubular capillaries.

2. Description of Background Information

In 1974, Pretorius, et al. (J. Chromatogr., 99, 23) described the concept of electroosmosis which they stated to be the flow of a liquid, in contact with a solid surface, under the influence of a tangentially applied electric field. They attributed the electroosmotic flow to the formation of an electric double layer, at the solid-liquid interface, due to the preferential adsorption of ions on the surface. This transport process can be visualized with reference to FIG. 1. In FIG. 1, a small bore double open-ended tube 10 is shown in cut away cross section. The tube is filled with a conductive liquid 11 sometimes referred to herein as a "support electrolyte". The wall of tube 10 contains preferentially adsorbed positive ions 12. (Depending upon the material of tube 10, the adsorbed charge could be negative, instead.) Positive ions 12 attract anions 13 from conductive liquid 11 and set up an electric double layer 14. This preferential attraction of anions to the wall results in a net excess positive charge in the body of liquid 11. Thus, when an electric potential is applied, such as a 30 kV potential between electrodes 15 and 16, located at the ends of the column of liquid 11 contained within tube 10, the positively charged liquid moves toward the cathode. Pretorius et al. proposed the use of this process in thin-layer and high speed liquid chromatography settings.

In 1979, Mikkers, et al. (J. Chromatogr. 169, 11) described the use of narrow-bore (e.g. 0.2–0.35 mm i.d.) tubes for high performance zone electrophoresis. More recently, J. W. Jorgenson and K. D. Lukacs have reported (J. Chromatog. 218 (1981), 209; Anal. Chem. 53 (1981), 1298; and Science 222 (1983), 266) the use of 75 $\mu$m glass capillaries to carry out such separations. Tsuda, et al, reported similar work in J. Chromatog. 248 (1982), 241 and J. Chromatog. 264 (1983), 385. An advantage to the use of capillary channels is that joule heating effects which disturb the sample flow are minimized.

The separation process relies upon the electroosmosis effect just described and upon the differential effect of the electric field on solutes in the liquid medium depending upon their positive, neutral or negative charge. These related effects may be visualized with reference to FIG. 2. FIG. 2 is a copy of FIG. 1 but with various charged species 18 and 19 in liquid 11. Cationic species 18 is electrophoretically drawn toward cathode 16. Anionic species 19 is electrophoretically repelled by cathode 16. As is shown in FIG. 2, and as is usualy the case, the velocity of the liquid 11 is larger than the electrophoretic velocities of the species in solution such that all the species can be seen to move in the direction of the electroosmotic flow but at differing rates. The combination of electroosmotic flow and electrophoretic movement is referred to in the literature and herein as electrokinetic movement, and a separation which relies upon these two effects is referred to as an electrokinetic separation.

Moreover, electroosmotic flow has plug flow characteristics as opposed to laminar flow characteristics. This favors high resolution separations. One can, in theory, use an electrokinetic separation to provide separation of species in solution, and one should in principle be able to detect these separations. However, as stated by Jorgenson and Lukacs in the conclusion of their Science review article, "The greatest obstacle to further development and utilization of capillaries [in such separation methods] is the requirement of extremely sensitive detection, and more types of detection with higher sensitivity are greatly needed." The types of detectors used heretofore to indicate the presence of species as they move through electrokinetic separation columns have included UV absorption and conductivity used by Mikkers, et al; on-column fluorescence detection with lamp excitation used by Jorgenson and Lukacs and UV absorption detection used by Tsuda, et al. David, et al, of the Oak Ridge National Laboratory in research report ORNL/TM-9141 in contract W-7405-eng-26 have disclosed an on-column lamp-excited fluorescence detector system and its use in connection with a capillary electrophoresis system. The selection of a suitable detection system is rendered more difficult by the practical consideration of operator safety when high voltages are present. With electric potentials in the range of several tens of thousands of volts passing through the sample as it is being measured, the detector must be reliable and require no operator manipulation in or directly around the sample.

It is an object of the present invention to provide an improved detection method and system sought by the art. It is a further object of this invention to provide new and more sensitive electrokinetic assay methods by employing this improved detection method and system.

STATEMENT OF THE INVENTION

It has now been found that the detection of electrokinetically-transported target species as said species pass in a support electrolyte through a detection volume can be carried out with improved efficiency when the detection event associated with the passage of the species through the detection volume is a change in emitted light, in particular fluorescence, which emitted light has been generated by a beam of electromagnetic radiation supplied on-column by a coherent source. The use of a coherent radiation source permits the radiation of a well-defined wavelength to be delivered on-column to the sample without hazard and without appreciable loss of intensity and without unwanted interference from scattered light, as compared to incoherent light sources. The use of coherent radiation increases sensitivity because interference from Raman and Rayleigh scattering is minimized. This detection system allows mixtures of compounds to be analyzed and/or separation with improved efficiency. It is possible, using the detection system of this invention to detect amounts of targets in the range of a femtomole ($10^{-15}$ moles) or less.

In an additional aspect, this invention provides a detector for use with electrokinetic separation processes. This detector includes an on-column coherent excitation source for fluorescence analysis.

Another aspect of this invention is the electrokinetic separation of racemic mixtures into their optically active constituents which occurs when an optically active (i.e., chiral) support liquid is used in the electrokinetic separation process.

DETAILED DESCRIPTION OF THE INVENTION

DESCRIPTION OF PREFERRED EMBODIMENTS

Figure 1:
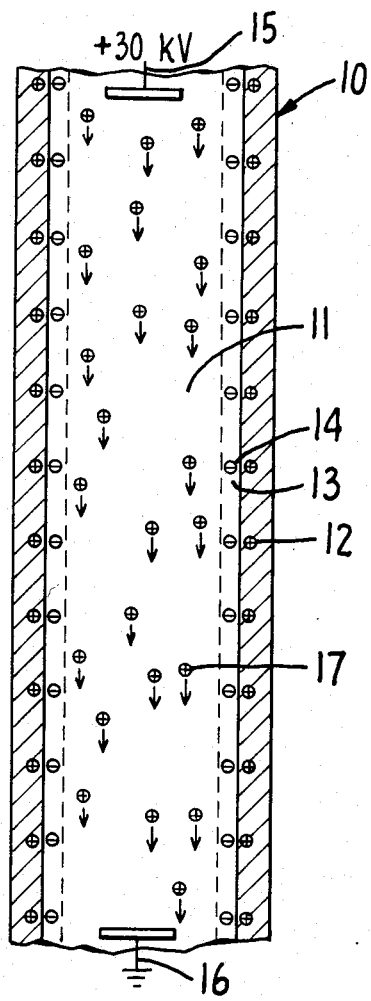
FIG. 1 is a cross-sectional view of a liquid-filled tube illustrating the process of electroosmotic pumping.
Figure 2:
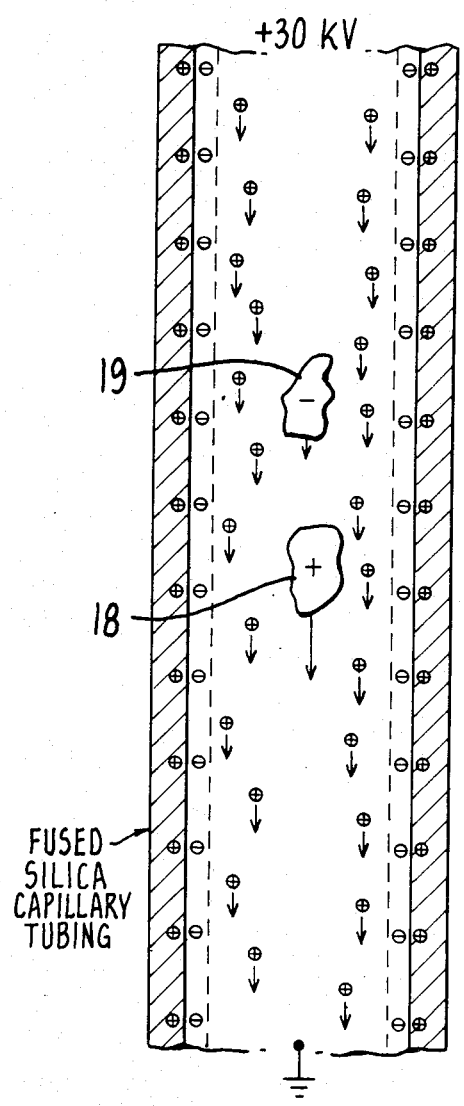
FIG. 2 is a cross-sectional view of a liquid-filled tube illustrating the process of electrokinetic separation.

The present invention will be first described by the following examples. These examples are provided to illustrate one mode for practicing the present invention and are not to be construed as limiting the scope of the invention as defined by the appended claims.

EXAMPLE 1

An electrokinetic separation system employing a laser-excited fluorescence detector was constructed. This sytem will be described with reference to FIGS. 3 and 4. The system included a fused-silica capillary 30 (Hewlett-Packard Co.) which was 75 cm in total length and which had a 75 $\mu$m inside diameter. The capillary had an opaque polyimide protective coating 31 on its outer surface, a section of which was removed with flame to give a translucent section 32. Capillary 30 was liquid-filled with a support electrolyte containing 5 mM l-histidine, 2.5 mM $CuSO_4.5H_2O$ and 10 mM ammonium acetate adjusted to pH 7-8 by the addition of $NH_4OH$. Feed container 34 and outflow container 35 contained support electrolyte as well, so that liquid-filled capillary 30 created a continuous liquid and electrical connection between them. A $-30$ kV potential from power supply 36 was applied across electrodes 37 and 39 by means of wires 40 and 41, respectively, and gave a complete electrical circuit. The inner surface of capillary 30 was such as to preferentially adsorb positive ions; this caused cations in the electrolyte to be preferentially drawn to the capillary wall as a double layer and in turn imparted a net positive charge to the body of the support electrolyte in capillary 30. When a $-30$ kV potential was applied to the liquid in outflow conductor 35 by electrode 39, it caused this positively charged liquid to be electroosmotically drawn from capillary 30 into container 35 and to draw additional electrolyte out of container 34 into capillary 30. The current flow was 30-33 $\mu$A. The linear velocity of liquid through capillary 30 was about 1-2 mm/second.

Capillary 30 passed through flow cell 42 and was held in position by fittings 44 and 45 with translucent section 32 which defined a detection volume in the center of flow cell 42.

Flow cell 42 included an on-column fluorescence detector which used a helium-cadmium laser 46 (Liconix, Model 4240B, Sunnyvale, CA) having a 5 mW continuous wave output at 325 nm wavelength as excitation source. The filtered output of the laser was focused via lens 47 on optical fiber 49 (80 $\mu$m fused silica material) which carried the beam of laser light into flow cell 42. Fiber 49 was held in position by a 3-axis positioner head 50 with its output focused on translucent section 32 of capillary 30. Fluorescence emanating from the fluid being transported through the detection volume was collected perpendicular to the excitation beam by a 0.6 mm fused silica optical fiber 51. Fiber 51 was held in position by 3-axis positioning head 52. The fluorescence collected with fiber 51 was passed through a high pass cut off filter 53 and a fast monochromator 54 (Centronic Model Q 4249B) which served to select a variable wavelength bandpass, and a photomultiplier 55, the output of which was amplified by means of a Keithly Instruments Inc. Model 480 picoammeter (not shown) and fed through line 56 to stripchart recorder 57.

In use, a sample was injected into capillary 30. This was accomplished by dipping the anode end of capillary 30 into the liquid sample contained in container 58, connecting anode lead 40 to electrode 59 and turning on the high voltage for a short period (5-10 seconds) at 6 kV. This caused a defined 1 to 5 mm long "plug" of sample to be drawn into column 30.

Figure 5:
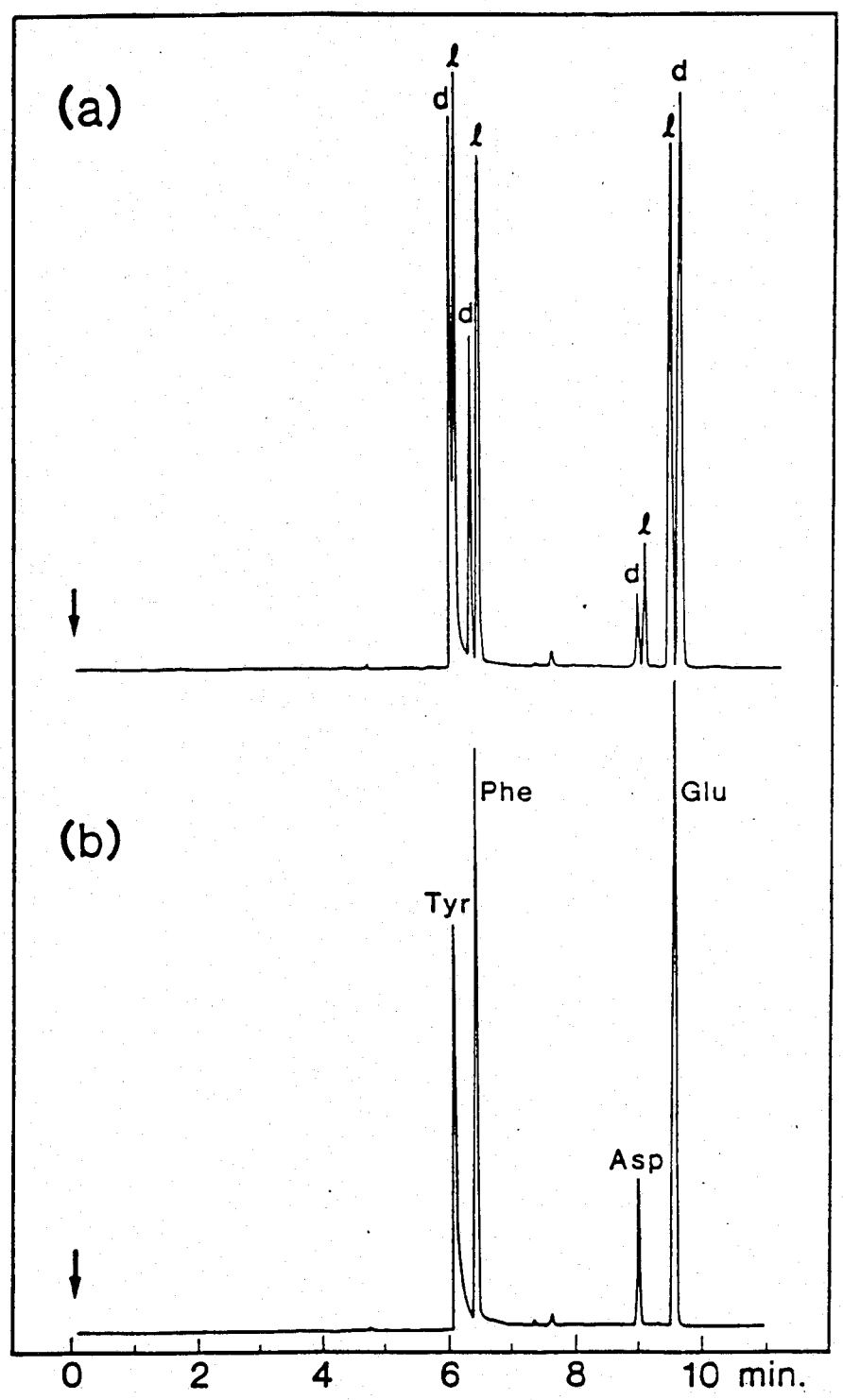
FIGS. 5a and 5b are two representative electropherograms showing separations achieved and detected using the present invention.

A first sample, made up of $10^{-4}$M of each of each of the following dansylated amino acids:

d-Tyr
l-Tyr
d-Phe
l-Phe
d-Asp
l-Asp
d-Glu
l-Glu was prepared in the same liquid used as the support electrolyte. The labeled amino acids were purchased from Sigma Chemical Co., St. Louis, MO, or prepared by the methods of Tapuhi, et al. (I), *Anal. Biochem.* 115, 123 (1981), and Tapuhi, et al. (II), *J. Chromatog.*, 205, 325 (1981). The support electrolyte liquid contained a copper-II complex with l-histidine. This complex is optically active and thus the support electrolyte was a chiral support electrolyte. As the four optically active pairs moved through column 30, they were separated from one another. Also, separation occurred between the members of each pair of optical isomers. As each of the eight separated species passed through the detection volume they were detected. In this case, their dansyl labels emitted fluorescence which was detected. The results are shown in FIG. 5a as an electropherogram, in this case a plot of laser-excited fluorescence signal versus time. Then one half of the l-histidine in the support liquid was replaced with d-histidine so as to yield a 1:1 mixture of d- and l-histidine of equal total concentration to that used in the previous experiment. The experiment was repeated, using this nonchiral support electrolyte and no separation of the d and l isomers was observed. Four individual peaks were found, one for each amino acid, as shown in FIG. 5b. Similarly, when the l-histidine was completely replaced with d-histidine, separation occurred with the order of the dansylated d and l amino acid isomers being reversed.

These three experiments thus illustrated the broad aspect of this invention that measurement of changes in fluorescence excited on-column by a coherent (i.e. laser) energy source is an effect and efficient method to detect the presence of species separated in electroosmotically pumpable liquids in narrow bore channels by electrokinetic processes. These experiments used a detection volume of about 0.5 nanoliters. The species being detected had concentrations in the electrokinetically-pumpable support electrolyte of about $10^{-4}$ moles per liter. The signal to noise ratios observed were greater than 100:1. Combining these factors, one finds that the present detection system can detect $5 \times 10^{-16}$ moles (that is, less than a femtomole) of target species.

These experiments also illustrate another aspect of this invention which is that electrokinetic separation processes can be used to separate optical isomers. It is believed that this separation of optical isomers is unprecedented both in terms of speed and in terms of sensitivity.

EXAMPLE 2

The experiment of Example 1 was repeated using a wider range of amino acids. The amino acids were used in various combinations. The results are listed in Table 1.

TABLE 1

Migration times ($t_d$, $t_l$). $\Delta t$ values [see Eq. (1)], and relative peak areas ($A_d$, $A_l$) for some d,l-dansyl-amino acids, taken under the conditions explained in the text at pH 8.0. The reproducibility for migration times is better than ±3% relative standard deviation (R.S.D.) units and for relative peak areas is about ±5% R.S.D.

| Amino Acid | $t_d$(min) | $t_l$(min) | $\Delta t \times 100$ | $A_d$ | $A_l$ |
|---|---|---|---|---|---|
| di-DNS-Tyr | 6.30 | 6.36 | −0.95 | 1.5 | 1.8 |
| DNS-Met | 6.75 | 6.71 | 0.63 | 1.6 | 1.6 |
| DNS-αAB[1] | 6.83 | 6.75 | 1.2 | 1.3 | 1.0 |
| DNS-Phe | 6.80 | 6.91 | −1.6 | 0.18 | 0.36 |
| DNS-Ser | 7.00 | 7.00 | 0.0 | 0.46 | |
| DNS-Val | 7.40 | 7.32 | 1.1 | 2.1 | 1.8 |
| di-DNS-Cys | 7.90 | 8.00 | −1.3 | 0.37 | 0.39 |
| DNS-Asp | 9.80 | 9.95 | −1.5 | 0.18 | 0.24 |
| DNS-Glu | 10.30 | 10.10 | 1.9 | 1.71 | 1.38 |
| DNS-Cys-Acid | 10.40 | 10.70 | −2.9 | 0.15 | 0.29 |

[1]N—dansyl-α-aminobutyric acid
[2]N—dansyl-cysteic acid

The excellent signal-to-noise ratios observed in Example 1 and illustrated in FIGS. 5a and 5b were again observed with this wider range of samples. The signal-to-noise ratio indicated that this wider range of labeled amino acids could be detected at femtomole ($10^{-15}$ mole) or lower levels by the present simple experimental arrangement. It is seen that baseline resolution is possible when the absolute magnitude of the quantity $$\Delta t = (t_d - t_l) / [\tfrac{1}{2}(t_d + t_l)] \qquad \text{Eq. (1)}$$

exceeds 0.01, where $t_d$ and $t_l$ are the migration times of the d and l optical isomers. Replacement of l-histidine by d-histidine in the support electrolyte reverses the migration order of the d and l amino acids, i.e., it changes the sign of $\Delta t$. FIG. 5a also shows that the fluorescence signals differ for the two optical isomers of the same dansyl-amino acid. In Table 1 the migration times, $\Delta t$ values, and relative peak areas referred to l-arginine as an internal standard for ten different d,l-dansyl-amino acids, are given. In all cases except d,l-serine, resolution is achieved, but the signs of $\Delta t$ varies with the amino acid. Although the migration order of the amino acids observed differs from that found in HPLC (see Lam, et al., *J. Chromatog.*, 199, 295 (1980), and *J. Chromatog.*, 239, 451 (1982), the migration order of the enantiomers, as shown by the sign of $\Delta t$, is the same.

Although not wishing to be bound by any particular theory of how the present invention works, chiral recognition with the Cu(II) l-histidine support electrolyte can be explained by mixed chelate complexation to form diasteromeric ternary complexes. The following explanation is consistent with all the present data. Amino acids bound to Cu(II) l-histidine migrate faster than free amino acids because the Cu(II) l-histidine carries positive charge under the pH conditions used. However, amino acids bound more strongly to Cu(II) l-histidine show a weaker fluorescence signal caused by quenching from association with the copper ion. Hence, the more complexed enantiomer migrates faster but shows a lower fluorescence signal caused by quenching from association with the copper ion (see FIG. 5a and Table 1).

EXAMPLE 3

Bovine insulin was labeled with fluorescein isothiocyanate (FITC). Ten milligrams of the insulin (Sigma Chemical Co.) were dissolved in 6 ml of 0.5M carbonate-bicarbonate buffer (pH 9.5). After the addition of 1.5 mg of FITC (Sigma Chemical Co.) the mixture was stirred overnight at 4° C. to couple the FITC to the insulin.

The reaction mixture was placed on a 1.5×40 cm Sephadex ™ C-25 silica gel filtration column and eluted with 0.01M phosphate-buffered saline of pH 7.4 at a flow rate of about 1 ml/minute. Unreacted FITC adsorbed to the silica gel. A yellow band containing FITC-labeled insulin was taken off the column and diluted with 5 parts of water. The zwitterionic buffer CHES (2-[N-cyclohexylamino]ethane sulfonic acid) was added to a 10 mM level which brought the pH of the solution to 9.

The solution of labeled insulin was used in the appartus of Example 1. Sample was placed on the capillary column by applying a 5 kV potential for 13 seconds. Then the sample was electrokinetically transported through the capillary using a 30 kV potential. Current flow was 5.6 milliamperes. On-column laser excitation was at 325 nm. Emission was monitored at 510 nm. Between 5.5 and 8.0 minutes, a group of peaks corresponding to the FITC labeled insulin were noted.

EXAMPLES 4 AND 5

The experiment of Example 3 is repeated twice with changes. In Example 4, in place of labeled insulin, the protein FITC-labeled concanavilin A (available from Sigma Chemical Co. or Fluka Chemical Corp., Hauppauge, N.Y.) is used. The feed mixture placed on the capillary column contains 0.5 mg/ml of the protein and 20 mM of a buffer which holds the pH to 8. Peaks corresponding to the electrokinetically labelled protein would be observed 5 to 10 minutes after the electrokinetic voltage is applied.

In Example 5, in place of labelled insulin, FITC-conjugated goat antihuman gamma globulin in phosphate buffered saline (pH 7.2) (available from Sigma Chemical Co.) is used. Again, fluorescent peaks caused by the transport of this immunoglobulin through the detection zone would be observed using the on column laser excitation method of this invention.

The invention is, of course, not limited to the embodiments just depicted. It can employ any configuration of narrow bore elongate walled channel in place of the capillary described above. In general terms, it is preferred to use a channel that is not more than about 500 μm across. Wider channels can give rise to excessive heating when the electrokinetic potential is applied. Preferred channels contain one or a plurality of channels each of which is up to about 500 μm across, especially from about 5 μm to about 350 μm across. It will be appreciated, that the smaller the cross section of the channel, the smaller the volume in the detection zone and thus the greater need for sensitivity of the detection systems. Because of their ease of construction, circular cross-section capillaries are preferred.

The channel should be of a length that is effective to achieve separation of species under the electrokinetic forces. It will be appreciated that the longer the channel the greater the time a sample will take to move through the channel and the greater the distance that the various species will be separated from one another. At the same time band broadening takes place so that resolution is not improved by adding length. These factors suggest practical limits to the channel length, although longer or shorter lengths could be used if desired. For example, good results are achieved with channel lengths as short as about 5 cm. Similarly, the transport time through a channel becomes inconveniently long for many routine analytical settings with channel lengths longer than several meters. Generally, channel lengths of from about 10 cm to about 200 cm, and especially from about 40 cm to 150 cm are preferred. Of course, longer and shorter channels, for example up to 4 or 5 meters or down to about 5 cm, can be used without departing from the spirit of this invention.

The elongate channel is constructed of a material that has the properties of being durable and retaining its physical integrity in contact with the support electrolyte, of being substantially nonconductive so as to conduct negligible electricity and to generate negligible heat as the electrokinetic potential is applied to it, and of being able to take on a positive or negative charge on its inner surface. A suitable material will have a conductance such that preferably at least about 95% of the conductance of the channel and its contained electrolyte is through the electrolyte. In addition, it is necessary that a portion of the channel is translucent so as to permit fluorescence to be emitted from the passing liquid contained in the channel for detection. The translucent portion of the channel can also be used, if desired, as a port for inputting the coherent excitation energy into the sample. It is possible to employ a separate translucent detection zone section to which the channel is joined, but this requires that the connection of the channel to the translucent section be carried out in a manner that does not lead to excessive heating or arcing when the electrokinetic voltage is applied across the connection or that does not lead to a disturbance in the liquid flow. One can avoid these problems by using a continuous channel with a translucent section inherent therein. Inorganic materials such as quartz, glass, and fused silica and organic materials such as teflon (polytetrafluoroethylene and fluorinated ethylene/propylene polymers), polychlorotrifluoroethylene, aramide, nylon (polyamide), polyvinylchloride, polyvinylfluoride, polystyrene, polyethylene and the like may be employed.

As pointed out herein in the Background of the Invention section, electroosmotic flow is achieved when the inner surface of the channel carries or adsorbs charged species. The inner surface can be modified to vary its charge such as by contacting the surface with an acidic liquid so as to impart more positive charges, or by contacting the surface with a basic material so as to impart more negative charges or by contacting the surface with a sylylating agent so as to reduce the number of charges. (See *Analytical Chemistry*, 53 No. 8, July 1981, 1298 for a description of the use of a trimethylsilane to reduce the charge density on the walls of a narrow channel electrophoresis zone and thus to vary the transport through the zone.) Other surface modification techniques that are known to the art may be used as well.

The voltage applied across the sample should be a voltage effective to cause discernable electrokinetic motion without excessive heating. Voltages below about 1000 volts are generally too low and voltages above about 100 kV are not commonly found in conventional high voltage power supplies. Based on these practical limits, voltages from about 3 kV to about 90 kV, and especially about 5 kV to about 60 kV, are preferred. The polarity of the electric potential determines the direction that the electrically charged species move. It is preferred for safety reasons to have as much of the analysis system at ground potential as possible.

The channel is filled with an electroosmotically pumpable support liquid. A liquid is electroosmotically pumpable when it is an electrolyte, that is, when it contains or carries enough electrically charged species to conduct an electric current. Typical electroosmotically pumpable support liquids contain, for example, at least about 0.0005 moles per liter of ionic species and preferably from about 0.001 to about 10 moles per liter of ionic species. Such levels provide high rates of electrokinetic transfer. Most commonly the support liquid is water-based or based on a mixed aqueous-organic liquid system. A mixed system can be useful to help solubilize or suspend organic target materials which have limited solubility in water alone. A neat organic liquid that is capable of conducting electricity can also be used. Representative materials for use in the support electrotype include water and mixed solvents made up of water admixed with one or more water-miscible organic materials such as lower (e.g. 1 to 4 carbon atom) alkanoic acids such as acetic acid, propionic acid, chloroacetic acid and the like; lower primary and secondary alkyl amines such as methyl amine, lower alcohols such as ethanol, methanol, and propanol; lower polyols such as the lower alkane diols; nitrogen containing liquids including acetonitrile, pyridine, piperidine and quinoline, lower ketones such as acetone and methyl ethyl ketone; lower alkyl amides such as DMF, N-methyl and N-ethyl formamide, N-ethyl acetamide and the like. These materials are merely representative. In practice any liquid which is itself an electrolyte or which can carry ionic species so as to be conductive may be used. With any of these liquids, the support liquid may contain added ionic materials such as salts, chelates and other complexes, acids, bases, buffers and the like. It is often preferred to use added ionic species which are zwitterions at the pH at which the liquid is passing through the electrokinetic channel. Representative materials include alkali metal and alkaline earth metal and transaction metal salts of inorganic acids; similar salts of organic acids, ammonium and organic base salts of such acids; halogen acids, organic acids, and other acids; metal acids and hydroxides, amines and other bases, and the like. Typical zwitterions include amino acids and the Good's buffers marketed by Sigma Chemical Company, St. Louis, MO. These added ionic or ionizable materials may be selected from these broad classes generally at will so long as they are compatible with the other components of the sample and the support electrolyte as their primary function is to increase the conductivity of the support electrolyte.

In one application, the present invention separates and detects the separation of mixed chiral compounds into enantiomers by the use of a chiral support electrolyte. A chiral support electrolyte is a liquid which meets the above-described criteria but also has the property of containing one or more chiral species which will preferentially interact with one member of the mixture of enantiomers causing it to preferentially acquire a different electrokinetic mobility than the other members of the mixture. The modification of electrokinetic mobility can take the form of preferentially associating a charged species with one enantiomer. It can also take the form of changing the charge density of one of several charged enantiomeric species by preferentially associating unchanged bulking groups with it or preferentially associating groups which vary one enantiomer's ability to combine with or attract charged species from the support electrolyte. A variety of materials useful as chiral support electrolyte components have been described in other settings in the literature. See, for example, the book *Enantiomers, Racemates, and Resolutions* by J. Jacques, et al., John Wiley & Sons, New York, 1981, which is incorporated herein by reference. Suitable chiral species for inclusion in a chiral support electrolyte include, chiral anions, for example, anions of (+) camphor-10-sulfonic acid, (+) camphoric acid, (−) dibenzoyltartaric acid, (+) and (−) d-(2,4,5,7-tetranitrofluorenylideneaminooxy)propionic acid (TAPA, diacetonekelogulonic acid, (+) and (−) mandelic acid, (−) malic acid (+) and (−) tartaric acid, (+) and (−) 3-bromocamphor-9-sulfonic acid and the like; chiral cations, for example cations of brucine, quinine, strychnine, (+) and (−) ephedrine, (−)-2-amino-1-butanol (+) and (−) d-methylbenzlamine, (+) and (−) ephedrine and the like; chiral complexes such as the copper II and zinc II complexes of 1-aspartyl-1-phenylalanine methyl ester (the commercially available artificial sweetener, aspartame), copper II complexes with 1-proline, 1-histidine and 1-pipecolic acid and zinc II complexes of L-2-alkyl-4-octyldiethylenetriamine, and the like.

The foregoing list of chiral species for inclusion in the chiral support electrolyte is merely representative. Any other chiral species which preferentially interacts with one member of the group of materials sought to be resolved and thereby varies differentially the electrokinetic mobility of the members of the group of materials may be employed as well. In selecting chiral species for inclusion one can often advantageously follow the teachings in the art relating to resolution of enantiomeric mixtures, in particular the teaching relating to such resolutions by formation of diastereoisomers.

The present invention employs detection of laser-excited fluorescence to determine the presence of electrokinetically-transported target species. The terms "fluorescent" and "fluorescence" are used broadly herein so as to include long- and short-lived photoluminescent species—that is, to include materials which might be thought of as "phosphorescent" or "fluorescent", and to include emissions which might be considered to be "phosphorescence" or "fluorescence".

Figure 3:
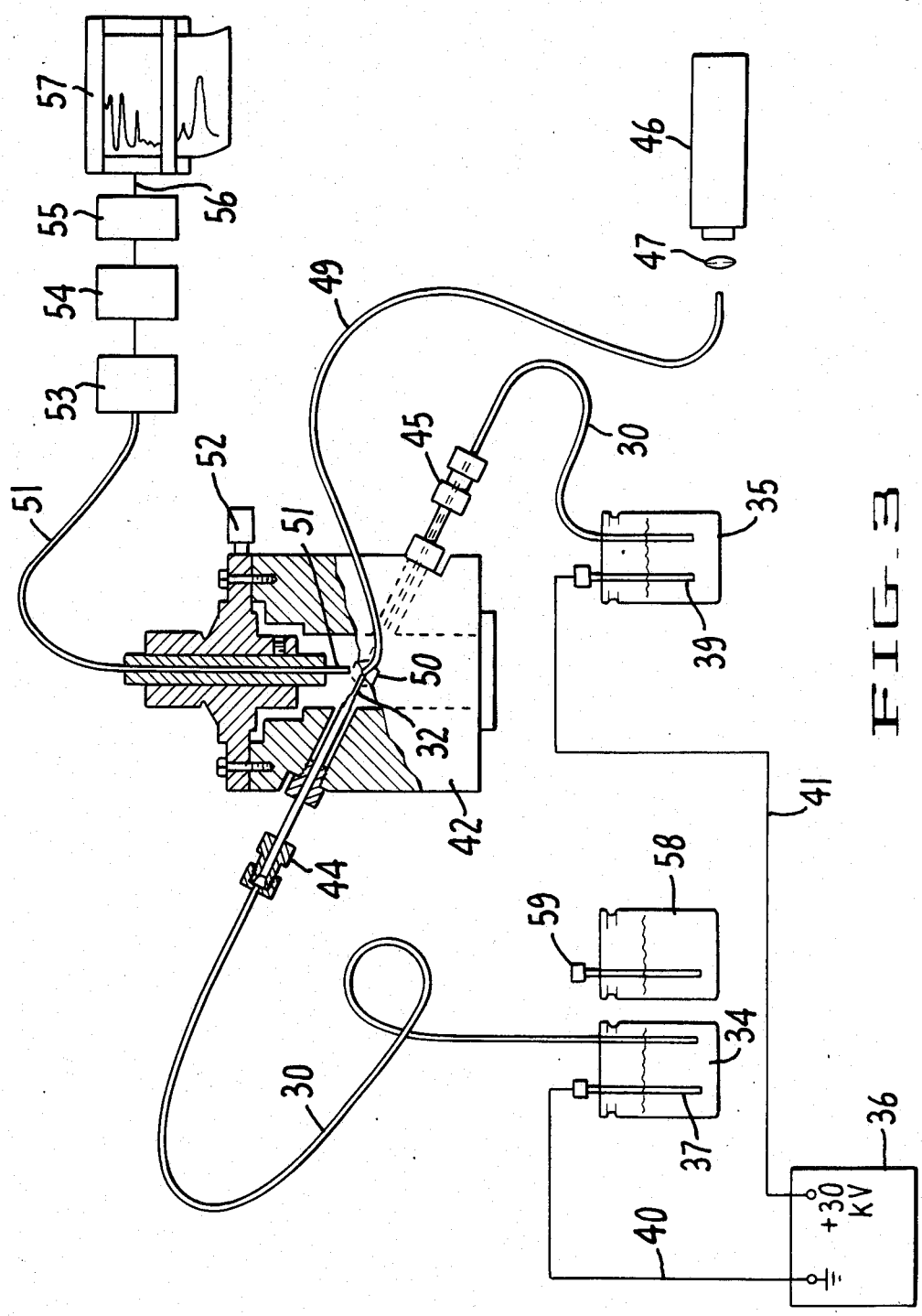
FIG. 3 is a partially schematic block diagram and partially cross-sectional view of one type of apparatus for carrying out the present invention.
Figure 4:
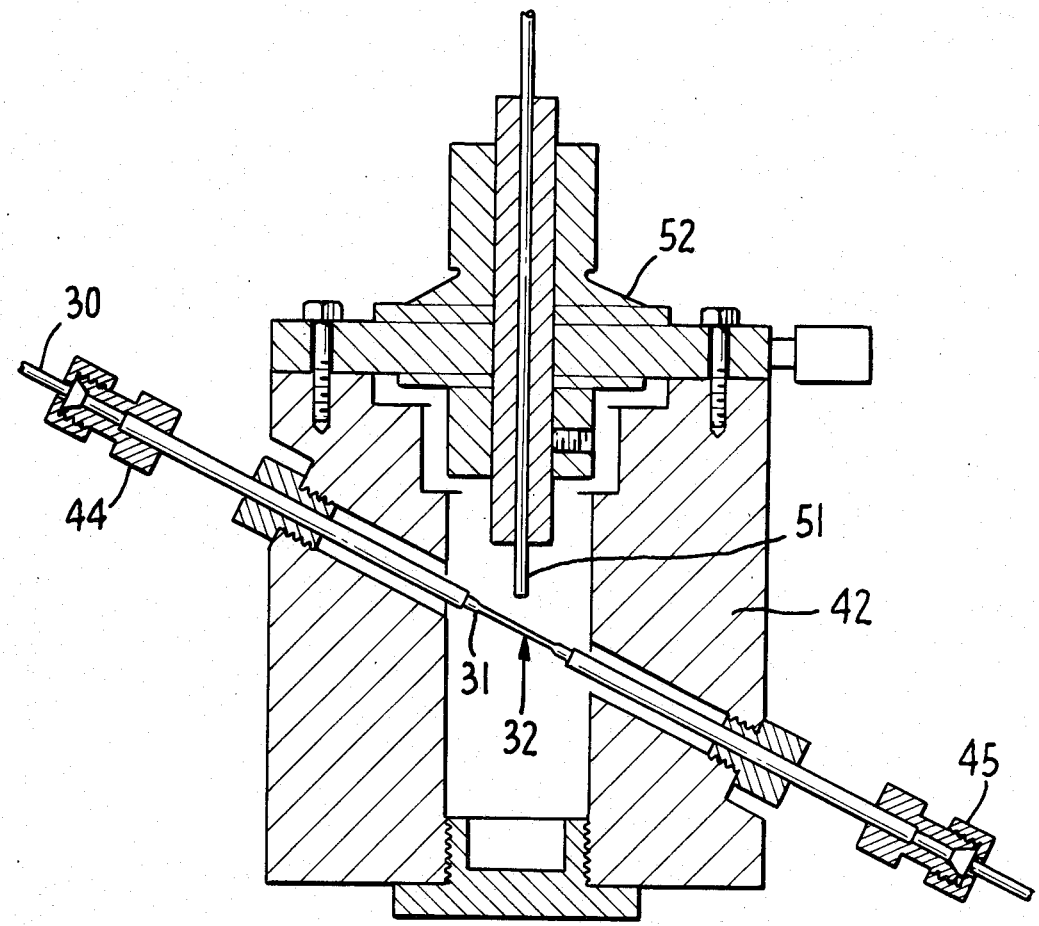
FIG. 4 is a cross-sectional view of an on column optical fluorescence-measuring cell for use in accord with the invention.

The change in emitted fluorescence which is detected can be an increase in fluorescence as would occur if a fluorescing target species traverses the detection zone. The change can be a decrease in fluorescence as would occur if a quenching or "transparent" species traverses the detection zone in the presence of a fluorescing background (See, H. Small, et al., *Anal. Chem.*, 54 (1982), 462–469.) It could also be a change in the spectral or temporal characteristics of the fluorescing species. The change in emitted fluorescence spectrum which is detected can be a change in the intensity of fluorescence in a particular acceptance wavelength band resulting from a target species transiting the detection zone and having a fluorescence which has been shifted into or out of the particular acceptance wavelength zone. Such a wavelength shift can result from intramolecular associations within the target species and the like. As shown in FIG. 3 this acceptance band can be easily defined by a wavelength band pass filter such as a high pass cut-off filter and a fast (high light throughput) monochromator. A change in temporal characteristics can be an increase or decrease in fluorescence lifetime, for example. It could also be a change in the polarization or angular distribution of the fluorescence which is shown to be a analytically significant effect by M. Jolley, *J. Anal. Tox.*, 5 (Sept/Oct 1981), 236.

While any of the above-described changes in fluorescence or their equivalents can be used as the detected event, the most commonly studied change in fluorescence—and thus, the change that is preferred in the present invention—is the increase in fluorescence that occurs when a fluorescent species traverses the detection zone. In some cases the target species being measured may be inherently fluorescent, but generally a fluorescent label is covalently attached or otherwise associated with the target species. The fluorescent label can be attached or associated with the target species when the sample is placed in the electrokinetic channel. Alternatively, the fluorescent label and the target species could interact during the species' passage through the electrokinetic channel. This interaction during passage can involve reaction of the target species with a material in the support liquid or within the electrokinetic channel walls. It could also result from an electrochemical reaction involving the target species. In any event, it is within the purview of this invention to use any combination of targets, labels and conditions so long as the target electrokinetically moves through a detection zone and the detection event is a change in coherent-radiation-excited fluorescence.

A wide range of fluorescent labels are well known. Representative common fluorescent labels include materials containing such primary functionalities as 1- and 2-aminonaphthalene, p,p'-diaminostilbenes, pyrenes, quaternary phenanthridine salts, 9-aminoacridines, anthracenes, oxacarbocyanine, merocyanine, 3-aminoequilenin, perylene, bis-benzoxaazole, bis-p-oxazolyl benzene, 1,2-benzophenazin, retinol, bis-3-aminopyridinium salts, hellebrigenin, tetracycline, sterophenol, benzimidazolylphenylamine. 2-oxo-3-chromen, indole, xanthene, 7-hydroxycoumarin, phenoxazine, salicylate, strophanthidin, porphyrins, triarylmethanes, rare earth metal chelates, and flavin.

Individual fluorescent compounds which have functionalities for linking or can be modified to incorporate such functionalities include dansyl chloride, fluoresceins such as fluoroscein and fluoroscein isothiocyanate, 3,6-dihydroxy-9-phenylxanthhydrol, rhodamineisothiocyanate, N-phenyl 2-amino-6-sofonatonaphthalene, 4-acetamido-4-isothiocyanatostilbene-2,2'-disulfonic acid, pyrene-3-sulfonic acid, 2-toluidinonaphthalene-6-sulfonate, N-phenyl, N-methyl 2 aminonaphthalene-6-sulfonate, ethidium bromide, atebrine, auromine-O, 2-(9'-anthroyl)palmitate, dansyl phosphatidyl-ethanolamine, N,N'-dioctadecyl oxacarbocyanine, N,N'-dihexyl oxacarbocyanine, merocyanine, 4-(3'-pyrenyl)butyrate, d-3-aminodesoxyequilenin, 12-(9'-anthroyl)stearate, 2-methylanthracene, 9-vinylanthracene, 2,2'-(vinylene-p-phenylene)-bis-benzoxazole, p-bis[2-(4-methyl-t-pheyloxazolyl)]benzene, 6-dimethylamino-1,2-benzophenazin, retinol bis(3'-aminopyridinium) 1,10-decandiyl diiodide, sulfanaphtheylhydrazone of hellebrigenin, chlortetracycline, N-(7-dimethylamin-4-methyl-2-oxo-3-chromenyl)maleimide, N-[p-(2-benzimidazolyl)-phenyl]maleimide, N-(4-fluoranthyl)maleimide, bis(-homovanillic acid), resazarin, 4-chlor-7-nitro-2,1,3-benzooxadiazole, merocyanine 540, resorufin, rose bengal, polyamine polyacid complexes of europium and terbium, and 2,4-diphenyl-3(2H)-furanone.

Desirably, fluorescing species should absorb light above about 200 nm, preferably above 300 nm and more preferably above about 400 nm, usually emitting at wavelengths greater than 10 nm higher than the wavelength of the coherent light absorbed. The fluorophore can be joined to the target covalently or noncovalently, directly or indirectly. When bonded covalently, the particular linking group will depend upon the nature of the two moieties to be bonded and their respective functions. A large number of linking groups and methods for linking are taught in the literature.

Binding can also be achieved by the use of receptors. For instance, an antigen fluorophore may be bound to a target through the intermediacy of a receptor, e.g., antibody, for the antigen. The receptor in turn may be bound covalently or noncovalently, e.g., through adsorption.

The target molecules which are separated and measured using the present invention can be selected virtually without limitation from the materials which can be fluorescently labeled and suspended or dissolved in the support liquid. Most commonly, target species will be material of biological or ecological or chemical interest.

The target molecules can be macromolecules such as polyamino acids, i.e., polypeptides and proteins, polysaccharides; nucleic acids and oligonucleotides such as RNA, DNA and DNA fragments, and combinations thereof. Such combinations of assemblages include bacteria, viruses, chromosomes, genes, mitochondria, nuclei, cell membranes, and the like.

The wide variety of proteins and polypeptides grouped according to similar structural features, proteins having particular biological functions, proteins related to specific microorganisms, particularly disease-causing microorganisms, etc.

The following are classes of proteins related by structure: protamines, histones, albumins, globulins, scleroproteins, phosphoproteins, mucoproteins, chromoproteins, lipoproteins, nucleoproteins, glycoproteins, proteoglycans, unclassified proteins, e.g., somatotropin, prolactin, insulin, and pepsin.

There are, of course, numerous potential target proteins found in the human plasma which are important clinically and include: prealbumin, albumin, $\alpha_1$-lipoprotein, thyroxin-binding globulin, Gc-globulin (Gc 1-1, Gc 2-1, Gc 2-2), chlinesterase, myoblobin, transferrin, fibrinogen, immunoglobulin G (IgG), immunoglobulin A (IgA), immunoglobulin M (IgM), immunoglobulin E (IgE) or $\gamma$E-globulin ($\gamma$E), complement factors, blood clotting factors, peptide and protein hormones including, for example, parathyroid hormone (parathromone), insulin, glucagon, somatotropin (growth hormone), follicle-stimulating hormone, luteinizing hormone (interstitial cell-stimulating hormone), gonadotropin, secretin, and gastrin.

Other macromolecular target materials of interest are mucopolysaccharides and polysaccharides derived from or present in microorganisms such as coliform bacteria, salmonellae, shigellae, proteus species, pasteurellae, brucellae, aerobic spore-forming baccilli, anaerobic spore-forming bacilli, mycobacteria, actinomycetes (fungus-like bacteria), spirochetes, mycoplasmas, and the like.

Other target species can include: rickettsia (bacteria-like parasites), chlamydia, fungi, and viruses, including adenoviruses, pox viruses, myxoviruses, reoviruses Types 1-3, hepatitis viruses. and tumor viruses.

The monomeric or smaller targets will generally be from about 75 to 20,000 molecular weight, more usually from 100 to 3,000 molecular weight. The targets of interest include drugs, metabolites, pesticides, pollutants, and the like. Included among them are the alkaloids such as morphine alkaloids (morphine, codeine, heroin, cocaine, benzoyl ecgonine, etc.), ergot alkaloids, steroid alkaloids, and the like.

Other drugs of interest include steroids, which include the estrogens and androgens; andrenocortical steroids; bile acids; cardiotonic glycosides; and aglycones, which include digoxin and digoxigenin; the barbiturates, e.g., phenobarbital and secobarbital; aminoalkylbenzenes, which include the amphetamines; cannabinal and tetrahydrocannabinol, vitamins, prostaglandins, antibiotics, nucleosides and nucleotides.

Another group of target compounds is amino acids and small peptides which include polyiodothyronines, e.g., thyroxine, and triiodothyronine, oxytocin, ACTH, angiotensin, met- and leu-inkephalin, their metabolites and derivatives.

The fluorophore can be attached to the target species by replacement of a hydrogen or other replaceable functionality on the target with a bond or linking group. The groups on the target can include hydroxyl, amino, aryl, thio, olefin, etc. The linking group will normally have from 1-20 atoms other than hydrogen. These atoms are generally carbon, oxygen, sulfur, nitrogen, and halogens of atomic number 17-35. The linking functionalities present in the linking groups include carbonyl, both oxo and non-oxo, active halogen, diazo, mercapto, ethylene, particularly activated ethylene, amino, and the like. The number of heteroatoms (i.e., not hydrogen or carbon atoms) will generally range from about 0-6, more usually from about 1-6, and preferably from about 1-4.

For the most part, the linking groups will be aliphatic, although with diazo groups, aromatic groups are involved. Generally, the linking group is a divalent chain having about 1-10, more usually from about 1-6 atoms in the chain. Oxygen will normally be present as oxo or oxy, bonded to carbon and hydrogen, preferably bonded solely to carbon, while nitrogen will normally be present as amino, bonded solely to carbon, or amido, while sulfur would be analogous to oxygen.

Common functionalities in forming the covalent bond between the linking group and the molecule to be conjugated are alkylamine, amide, amidine, thioamide, urea, thiourea, guanidine, and diazo.

Linking groups which find particular application with conjugation to polypeptides are those involving carboxylic acids which may be used in conjunction with diimides, or as mixed anhydrides with carbonate monoesters, or as active carboxylic esters, e.g., N-hydroxy succinimide or p-nitrophenyl. Nitrogen analogs may be employed as imidoesters. Aldehydes can be used to form imines under reductive aminations conditions, e.g., in the presence of borohydrides, to produce alkylamines. Other non-oxo carbonyl groups which may be employed include isocyanates and isothiocyanates. In addition, active acyl groups may be employed, particularly bromoacetyl groups.

In most instances, the target will have one or more functional groups which may be employed as the site for linking the linking group. Particularly, hydroxy, amino and aryl groups, particularly activated aryl groups, find use. Also, oximes may be prepared from oxo functionalities and the hydroxyl used as a site for joining to a linking group, such as carboxymethyl.

The choice of linking group will vary widely, depending upon the functionalities which are present in the fluorophore, in the compound to which the fluorophore is to be conjugated, the nature and length of the linking group desired, and the like.

The present invention brings about separation of species based on their relative motion in an electrokinetic field. Species having the same charge as the net excess charge of the support electrolyte (see Background of the Invention) will tend to move faster than the support electrolyte. Uncharged species will move at a velocity of the support electrolyte, and materials of opposite charge will move slower than the support electrolyte.

The conditions of the separation are very nonevasive. This makes it possible to use other propensities of species to achieve separations. For example, one can selectively associate a species with another charged species so as to impart charges to the first species. This can be carried out by matching hydrophobicity of the two species, for example, by forming a micellular dispersion of a first charged material and then preferentially associated the second uncharged material with the micelles. This would, in effect, impart charge to the second material. In another technique, one could vary the pH of the mixture so as to preferentially protonate or deprotonate a species in the mixture and thus vary its electrokinetic mobility.

The invention uses a source of coherent radiation—i.e., a laser—delivered on column to excite the fluorescent species. A continuous or pulsed laser can be used. Good results are achieved with low to moderate power lasers such as up to about 20 watts. Higher power lasers can be used, if desired, but are not seen to offer advantages and potentially have the disadvantage of unnecessarily heating the sample. The wavelength of the coherent light source should be matched to the excitation wavelength of the fluorescing species being measured—that is, it should be a wavelength effective to excite fluorescence.

The use of coherent light offers significant advantages in that it can be efficiently conveniently delivered directly to the sample channel by lenses and mirrors but, more importantly, by fiber optics, as well.

The beam of coherent excitation energy can be applied to the sample across the sample flow or, if desired, it can be applied axially with or against the direction of liquid flow. The measurement of fluorescence is carried out using conventional measuring methods. These can be continuous measurements or intermittent, i.e., timegated, measurements. These measurements are carried out at some selected wavelength of the fluorescent emission. The measurement may be carried out at the same point on the sample channel as the excitation occurs or downstream from the point of excitation. Measurement may be advantageously downstream in the case of long-lived fluorophores (e.g., phosphorescent materials) or when the excitation is supplied copropogating or counterpropogating with the flow. The angles for excitation and detection may be coplanar or may be varied as desired to eliminate interference, reflections, and the like.

The signal generated by the fluorescence detector may be recorded and/or it may be used as a control signal. Recording can be carried out by standard chart recorders, and the like. The control signal could be used, for example, to open or close a valve so as to trap or collect the fluorescent species in a preparative environment.

We claim as our invention:

1. A fluoroassay method for detecting the presence of a target species in an electroosmotically pumpable fluorescible liquid sample which comprises:
   a. placing said sample into one end of an electroosmotically pumpable-liquid-full narrow bore double open ended walled channel having a cross section dimension of not more than 500 $\mu$m and having at least a section which is translucent;
   b. applying an effective electroosmotic pumping potential to said pumpable sample and pumpable liquid thereby transporting the sample through the channel;
   c. irradiating the sample with coherent radiation of a wavelength effective to excite fluorescence in said sample; and
   d. detecting a change in the fluorescence emitted through the translucent section of the channel as the target species moves past the translucent section.

2. The method of claim 1 wherein said irradiating takes place through the translucent section of the channel.

3. The method of claim 1 wherein said coherent radiation is supplied to the sample as a beam by a fiber optic device.

4. The method of claim 1 wherein the electroosmotically pumpable liquid is an aqueous liquid.

5. The method of claim 1 wherein said walled channel is tubular.

6. The method of claim 1 wherein said target species is fluorescent and wherein the detected change is an increase.

7. The process for detecting the presence of each of a plurality of fluorescence-change-inducing target species in an electroosmotically pumpable fluorescible liquid sample which comprises;
   a. placing said sample into one end of an electroosmotically pumpable liquid-full narrow bore double open-ended walled channel having a cross section dimension of not more than 500 $\mu$m and having a length sufficient to effect electrokinetic separation of the plurality of species from one another and having after said length at least a section which is translucent; 1b. applying an effective electroosmotic pumping and electrophoretic separating potential to said pumpable sample and pumpable liquid thereby moving the sample through the channel and electrokinetically separating the plurality of target species from one another;

c. irradiating the sample as the sample moves past the translucent section with coherent radiation of a wavelength effective to excite fluorescence in said sample; and d. detecting a change in fluorescence in said sample emitted through said translucent section as the individual separated target species move past the translucent section of the channel.

8. The method of claim 7 wherein said irradiating takes place through the translucent section of the channel.

9. The method of claim 7 wherein said coherent radiation is supplied to the sample as a beam by a fiber optic device.

10. The method of claim 7 wherein the electroosmotically pumpable liquid is an aqueous liquid.

11. The method of claim 7 wherein said walled channel is tubular.

12. The method of claim 7 wherein each of the target species is fluorescent and wherein the detected change is an increase in emitted fluorescence.

13. A process for separating chiral compounds which comprises:

a. placing said compounds in an electroosmotically pumpable chiral support electrolyte, in an electrokinetic zone having a cross-section dimension of not more than 500 $\mu$m; and b. applying an effective electrokinetic potential to the support electrolyte in the zone for a period effective to separate the chiral compounds.

14. The process of claim 13 wherein said chiral support electrolyte contains a chiral species that reacts differentially with the chiral compounds being separated thereby imparting differing electrokinetic mobilities to the compounds being separated.

15. The process of claim 14 wherein said electrokinetic zone is an electroosmotically pumpable-liquid-full narrow bore double open ended walled channel.

16. A detector for indicating the presence of fluorescent species in a liquid sample comprising;

a. a narrow bore double open-ended walled channel having a cross-section dimension of not more than 500 $\mu$m for containing the sample at least a section of which channel is translucent;

b. means for irradiating the sample with coherent radiation of a wavelength effective to excite fluorescence in the fluorescent species; and c. means for collecting through the translucent section fluorescence emitted by the fluorescent species.

17. The detector of claim 16, wherein said channel defines an electrokinetic zone.

18. The detector of claim 17 wherein said channel is a tubular walled channel.

19. The detector of claim 17 wherein said means for irradiating comprise means for delivering a beam of coherent radiation through the translucent section.

20. A system for separating and detecting a plurality of fluorescence-change-inducing species in a sample including an electroosmotically pumpable liquid which comprises:

a. narrow bone double open-ended walled channel for containing an electroosmotically pumpable liquid said channel having a cross-sectional dimension of not more than 500 $\mu$m and being connected to and in communication with a translucent detection section;

b. means for feeding said sample into said channel;

c. means for supplying osmotically pumpable liquid to said channel before and after said sample is fed;

d. means for applying an effective electrokinetic potential along said channel and through said detection zone;

e. means for delivering to said sample as it passes through the detection zone coherent radiation of a wavelength effective to excite fluorescence in said sample; and f. means for detecting through the translucent section changes in emitted fluorescence as said fluorescence-change-inducing species transmit the detection zone.

* * * * *